(12) United States Patent
Li et al.

(10) Patent No.: US 9,050,022 B2
(45) Date of Patent: Jun. 9, 2015

(54) METHOD FOR DYNAMICALLY ANALYZING DISTRIBUTION VARIATION OF SCATTERERS AND APPLICATION USING THE SAME

(75) Inventors: Meng-Lin Li, Hsinchu (TW); Hao-Li Liu, Hsinchu (TW); Da-Wei Li, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 704 days.

(21) Appl. No.: 12/913,481

(22) Filed: Oct. 27, 2010

(65) Prior Publication Data

US 2011/0306880 A1  Dec. 15, 2011

(30) Foreign Application Priority Data

Jun. 15, 2010  (TW) .............................. 99119431 A (51) Int. Cl.
*A61B 8/00* (2006.01)
*A61B 8/08* (2006.01)
*A61N 7/02* (2006.01)
*A61B 19/00* (2006.01)

(52) U.S. Cl.
CPC ............ *A61B 8/08* (2013.01); *A61B 2019/5276* (2013.01); *A61N 7/02* (2013.01)

(58) Field of Classification Search
CPC ..................................... A61B 8/12; A61N 7/02
USPC ......................................................... 600/439
See application file for complete search history.

(56) References Cited

U.S. PATENT DOCUMENTS

2008/0114242 A1* 5/2008 Chang et al. ................... 600/443
2008/0154131 A1* 6/2008 Lee et al. ....................... 600/439

OTHER PUBLICATIONS

Chung-Kun Huang, Combination of Functional Ultrasonic Images to Evaluate the Tissue Ablation and Denaturation: a Feasibility Study, Jan. 1, 2010.*
Li, Da-Wei et al., "Detection of Focused-Ultrasound Induced Thermal Lesion by Ultrasonic Nakagami Imaging: A Feasibility Study", 2009 International Symposium on Biomedical Engineering combined with the Annual Scientific Meeting of Biomedical Engineering Society of R.O.C., Dec. 11, 2009, Taipei, Taiwan, R.O.C.

* cited by examiner

*Primary Examiner* — Tse Chen
*Assistant Examiner* — Hien Nguyen
(74) *Attorney, Agent, or Firm* — Muncy, Geissler, Olds & Lowe, P.C.

(57) ABSTRACT

A method for dynamically analyzing distribution variation of scatterers is provided and used for dynamically analyzing changes in two or three dimensional scatterer distribution and concentration of ultrasound data by using probability density function along with a moving window technique. The present invention has advantages in low computation load and may be used for real-time analysis. A method for dynamically detecting thermal ablation area and thermal ablation level and a method for dynamically controlling thermal ablation intensity are also provided for non-invasive detection and thermal ablation.

12 Claims, 11 Drawing Sheets

(5 of 11 Drawing Sheet(s) Filed in Color)

METHOD FOR DYNAMICALLY ANALYZING DISTRIBUTION VARIATION OF SCATTERERS AND APPLICATION USING THE SAME

BACKGROUND OF THE INVENTION

1. Field of the Invention

The present invention relates to a method for dynamically analyzing distribution variation of scatterers and application using the same, particularly to a method for dynamically analyzing distribution variation of scatterers by using probability density function and moving window technique and application using the same.

2. Description of the Prior Art

Non-invasive therapy has been highly regarded recently, and particularly, high-intensity focused ultrasound (HIFU) has been a novel tool in local thermal ablation and has great potential in developing as a supplementing surgery tool for lesion resection. However, clinical practitioners may have difficulty in determining thermal ablation area and extent by using conventional B-mode ultrasound image only and the risk during medication may be thus increased.

Integrated temperature and elasticity ultrasound images have been proposed for monitoring HIFU thermal ablation; however, the adopted algorithm is highly time-consuming and has limited capability in real time analysis.

US patent application No. 20080154131 disclosed a method for enhancement of visibility of ablation regions and includes obtaining input image data about an ablation region, wherein the image data comprises back-scattering intensity, and applying a dynamic gain curve based on the image data to obtain an output signal for use in enhancing the visibility of the ablation region. However, it can not achieve dynamic monitor and analysis on ablation area.

To sum up, it is now a current goal to develop a method for dynamically detecting and analyzing thermal ablation area.

SUMMARY OF THE INVENTION

The present invention is directed to a method for dynamically analyzing distribution variation of scatterers so as to dynamically analyze changes in two or three dimensional scatterer distribution and concentration of ultrasound data by using probability density function along with a moving window technique. The present invention has advantages in low computation load and may be used for real-time analysis.

According to one embodiment, a method for dynamically analyzing distribution variation of scatterers, including following steps: obtaining a first ultrasound data and a second ultrasound data of a sample in a sequential manner, wherein the first ultrasound data and the second ultrasound data respectively comprise a plurality of corresponding coordinates and a plurality speckles formed with a plurality of scatterers; defining a size of a window; calculating a statistical parameter for each of the coordinates with a probability density function, wherein the statistical parameter represents the statistical distribution for signal amplitude of the speckles within the window of each of the coordinates; and comparing the statistical parameter of each of corresponding coordinates of the first ultrasound data and the second ultrasound data to analyze the distribution variation of scatterers in the sample.

The present invention is also directed to a method for dynamically detecting thermal ablation area and thermal ablation level and a method for dynamically controlling thermal ablation intensity based on the above-mentioned detection of variation in scatterer distribution.

According to another embodiment, a method for dynamically detecting precise thermal ablation area and analyzing thermal ablation extent, comprises obtaining a first ultrasound data and a second ultrasound data of a thermal ablation area in a sequential manner, wherein the first ultrasound data and the second ultrasound data respectively comprise a plurality of corresponding coordinates and a plurality speckles formed with a plurality of scatterers; defining a size of a window; calculating a statistical parameter for each of the coordinates with a probability density function, wherein the statistical parameter represents the statistical distribution for signal amplitude of the speckles within the window of each of the coordinates; and comparing the statistical parameter of each of corresponding coordinates of the first ultrasound data and the second ultrasound data to analyze the distribution variation of scatterers in the thermal ablation area to detect the precise thermal ablation area and analyze thermal ablation extent.

According to yet another embodiment, a method for dynamically controlling thermal ablation intensity, comprises ablating a thermal ablation area with a thermal ablation device; obtaining a first ultrasound data and a second ultrasound data of a thermal ablation area in a sequential manner, wherein the first ultrasound data and the second ultrasound data respectively comprise a plurality of corresponding coordinates and a plurality speckles formed with a plurality of scatterers; defining a size of a window; calculating a statistical parameter for each of the coordinates with a probability density function, wherein the statistical parameter represents the statistical distribution for signal amplitude of the speckles within the window of each of the coordinates; comparing the statistical parameter of each of corresponding coordinates of the first ultrasound data and the second ultrasound data to analyze the distribution variation of scatterers in the thermal ablation area to detect the precise thermal ablation area and analyze thermal ablation extent; and controlling the intensity of the thermal ablation device based on the thermal ablation extent of the thermal ablation area.

Other advantages of the present invention will become apparent from the following descriptions taken in conjunction with the accompanying drawings wherein certain embodiments of the present invention are set forth by way of illustration and examples.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and many of the accompanying advantages of this invention will become more readily appreciated as the same becomes better understood by reference to the following detailed descriptions, when taken in conjunction with the accompanying drawings, wherein.

DESCRIPTION OF THE PREFERRED EMBODIMENT

One objective of the present invention is directed to analyzing the 2D or 3D distribution of scatterers in the ultrasound data by using PDF (probability density function) in combination with moving window technique.

PDF may be used for describing the probability distribution for random variables. The PDF of continuous random variables in statistics theory is used for describing a relative occurrence possibility of random variables at a specific point within an observing space.

As for moving window technique, the present invention defines a size of a window based on the resolution of the ultrasound image system, moves the window and calculates a statistical parameter within the scope of the window with a given PDF so as to calculate the statistical distribution for signal amplitude of the speckles within the window and analyze the variation in scatterer distribution.

Figure 1:
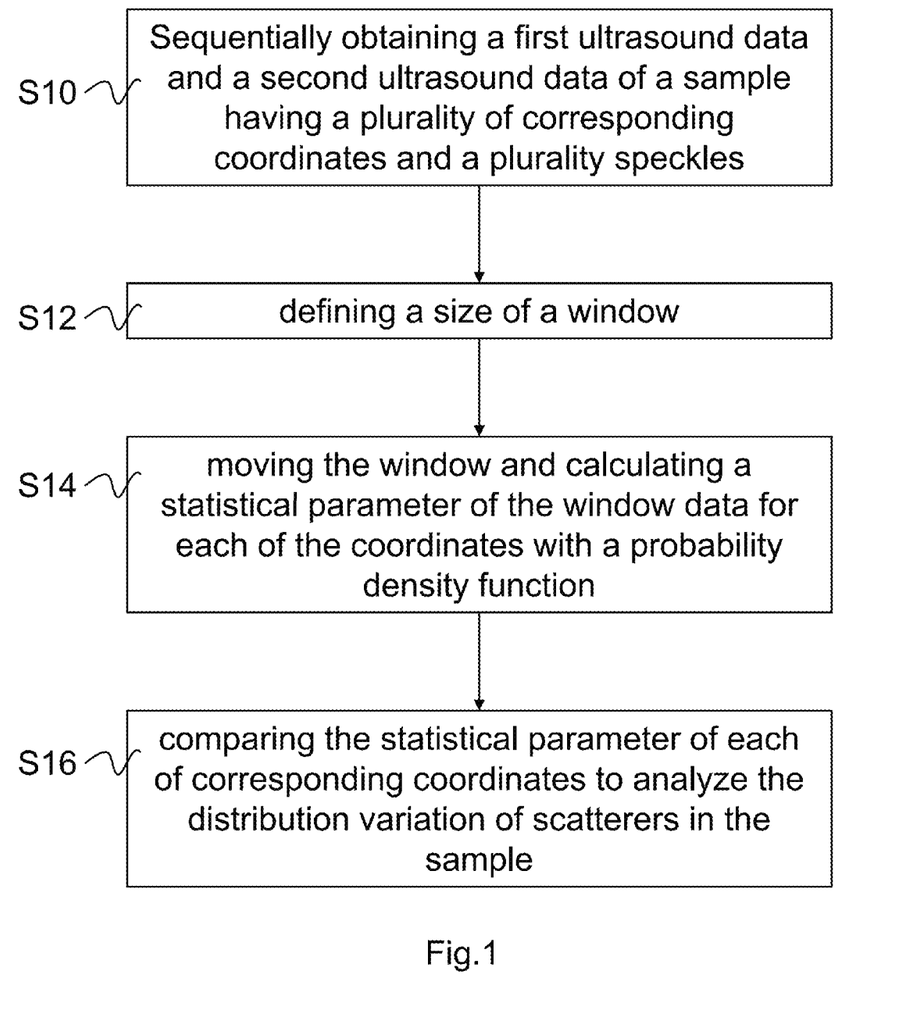
FIG. 1 is a flow chart illustrating a method for dynamically analyzing distribution variation of scatterers according to one embodiment of the present invention.

Some embodiments of the present invention are now further detailed. Refer to FIG. 1, which is a flow chart illustrating a method for dynamically analyzing distribution variation of scatterers according to one embodiment of the present invention. Firstly, at step S10, a first ultrasound data and a second ultrasound data of a sample are obtained in a sequential manner. The first ultrasound data and the second ultrasound data respectively include a plurality of corresponding coordinates and a plurality speckles formed with a plurality of scatterers.

The resolution of ultrasound data, particularly the first and second ultrasound data, is usually definite; therefore, the corresponding coordinates usually refers to the resolution of ultrasound data generated by an ultrasound system. Preferably, each coordinate is defined based on each pixel in resolution for following data processing. In another embodiment, coordinates in fixed intervals may be sampled and processed for enhanced system processing speed.

Speckles in ultrasound data are a plurality of points having different brightness to form the ultrasound data. Speckles are formed with scatterers which are where ultrasound traveling in the body tissues scattered. Due to the much smaller size of scatterers in comparison to ultrasound wavelength, scattering tends to occur where a number of unevenness presents. The diffractive sound waves generated by collision of ultrasound to scatterers travel in all directions, and the signal of the ultrasound image is mainly constituted with the backscattering waves diffracted back towards the original incident direction. Since the resolution of ultrasound images is definite and can not provide infinitesimal sampling size, the speckles are thus formed. To be specific, there're usually dozens of scatterers in one sampling size; therefore, the response generated with collision of the sound wave in the system to single scatterer has to be considered with other responses generated with other scatterers in the same sampling size, and the overall diffraction effect is presented by responses of these scatterers.

RF (radio frequency) data is the original data format of ultrasound data and may be converted, using baseband demodulation, into envelope data, which may be further processed into image data. The envelope data has an advantage in smaller data load than the RF data; therefore, the present invention adopts envelope data, which may be converted from RF data or image data, for ultrasound data processing. In addition, the ultrasound data may be a 2D or 3D ultrasound image.

Next, at Step S12, a size of a window is defined for performing moving window technique. It is noted that the dimension and shape of the window will influence the resolution and precision for PDF. To be specific, smaller window would provide better resolution but contain little packet information so that the precision of the estimated statistical parameter using PDF within the window area would be influenced; and larger windows would cause lowered resolution. Therefore, defining appropriate window size is a prerequisite for both of image resolution and statistical parameter precision. The optimized dimension and shape of the window would be later detailed in the example of the present invention.

At Step S14, a statistical parameter for each of the coordinates is calculated by using a probability density function, wherein the statistical parameter represents the statistical distribution for signal amplitude of the speckles within the window of each of the coordinates. There may be one or more statistical parameters, for example without limited to a mean value, a standard deviation value, and so on. Step S14 adopts PDF in combination of moving window technique to calculate the statistical parameter of the window data, in terms of the statistical distribution for signal amplitude of the speckles within the window of each of the coordinates. The common PDF includes without limitation to Nakagami distribution, Rayleigh model, Gaussian model, Blackman model or K-distribution model.

The scatterers may be classified into incoherent scatterers (which are randomly distributed) and coherent scatterers (which are periodically distributed) according to distribution property and may be interchanged because of light, heat, sound wave or other forms of energy so as to be varied in their scattering value, distribution and gradient and signal amplitude of speckles. The PDF of backscattering ultrasound signal from tissues may correspond to the number and distribution of the internal scatterers in the tissue. In other words, statistical distribution calculated from the backscattering echo signal may be used for characterizing and quantitating the tissue and provide great development and potential for clinical diagnosis.

At Step S16 for the last step, the statistical parameter of each of corresponding coordinates of the first ultrasound data and the second ultrasound data are compared to dynamically analyze the distribution and concentration variation of scatterers in the sample. The simplest comparison method for statistical parameters would be subtraction; however, other gaining method may be adopted for higher contrast. In addition, a reference value for statistical parameter may be defined, and the statistical parameter for each coordinate may be compared to the reference value for statistical parameter for comparing the difference. In one embodiment, a statistical parameter differential image is formed based on the comparison result of the statistical parameters of each of the corresponding coordinates so as to dynamically analyzing areas with variation in scatterer distribution.

The method of the present invention for dynamically analyzing distribution variation of scatterers may work in a real-time manner and is achieved by adopting PDF in combination of moving window technique to analyze the ultrasound envelope data. To be specific, due to less data load for envelope data in comparison to RF data and less computation load achieved by analyzing data contained within the moving window with moderate size, the overall computation load may be controlled and maintained at low level and real-time computation (more than 30 frames per second) may be achieved.

As will be appreciated by those of ordinary skill in the art, the foregoing example and process steps may be implemented by suitable code on a processor-based system, such as a general-purpose or special-purpose computer. Calculation of the above-mentioned moving window technique and PDF may be carried out with CPU (Central Processing Unit) or GPU (Graphics Processing Unit). It should also be noted that different implementations of the present invention may perform some or all of the steps described herein in different orders or substantially concurrently, that is, in parallel. Furthermore, the functions may be implemented in a variety of programming languages, including but not limited to C++ or Java. Such code, as will be appreciated by those of ordinary skill in the art, may be stored or adapted for storage on one or more tangible, machine readable media, such as on memory chips, local or remote hard disks, optical disks (that is, CD's or DVD's), or other media, which may be accessed by a processor-based system to execute the stored code.

Figure 2:
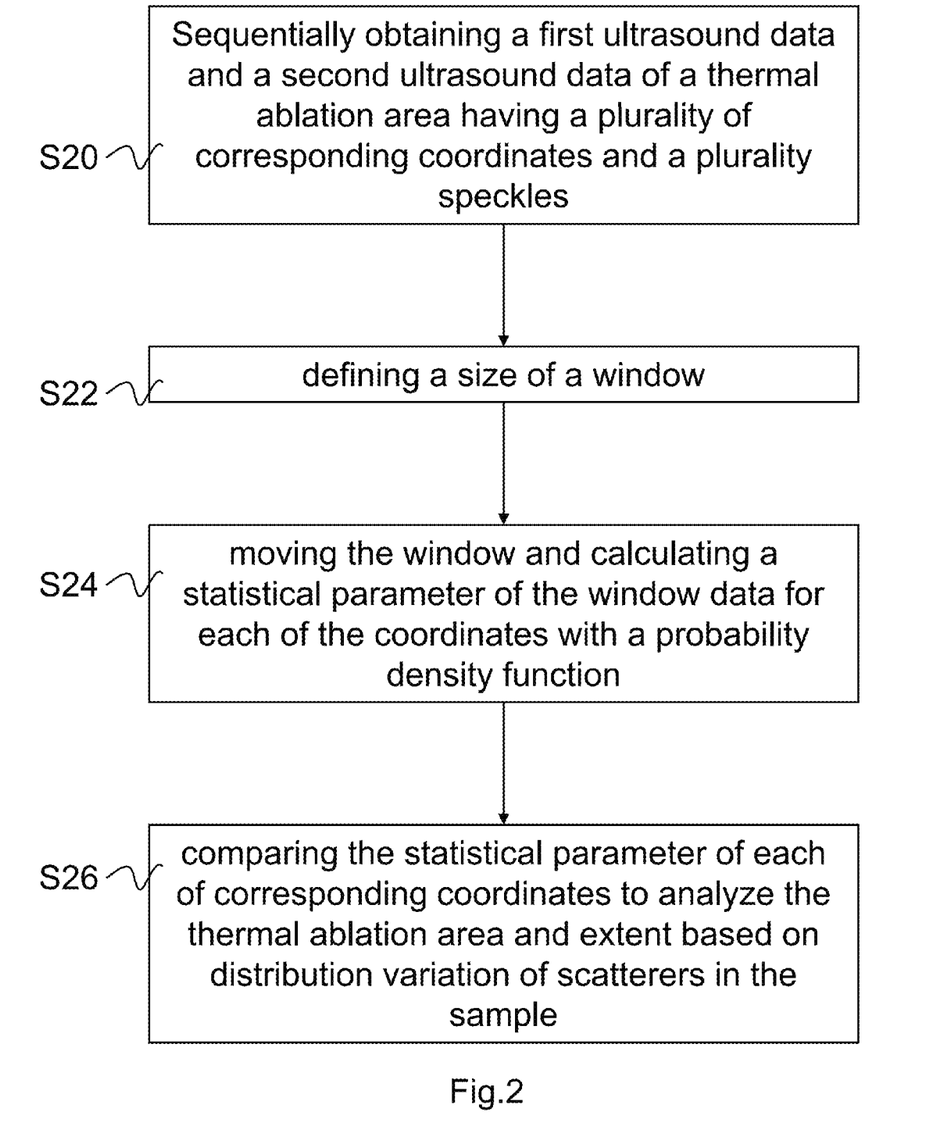
FIG. 2 is a flow chart illustrating a method for dynamically detecting precise thermal ablation area and analyzing thermal ablation extent.

As above-mentioned, the distribution and diffractive properties of scatterers may be changed because of heat or thermal ablation. Therefore, refer to FIG. 2, which is a flow chart illustrating a method for dynamically detecting precise thermal ablation area and analyzing thermal ablation extent. At Step S20, a first ultrasound data and a second ultrasound data of a thermal ablation area are obtained in a sequential manner, wherein the first ultrasound data and the second ultrasound data respectively comprise a plurality of corresponding coordinates and a plurality speckles formed with a plurality of scatterers. At Step S22, a size of a window is defined. At Step S24, a statistical parameter for each of the coordinates is calculated by using a probability density function, wherein the statistical parameter represents the statistical distribution for signal amplitude of the speckles within the window of each of the coordinates. At Step S26, the statistical parameter of each of corresponding coordinates of the first ultrasound data and the second ultrasound data are compared to analyze the distribution variation of scatterers in the thermal ablation area to detect the precise thermal ablation area and analyze thermal ablation extent. Also, a statistical parameter differential image is formed for comparison. Here, the thermal ablation area may contain bubbles or no bubbles and may be caused by chemicals (such as alcohols and liquid nitrogen), ultrasound or laser.

Figure 3:
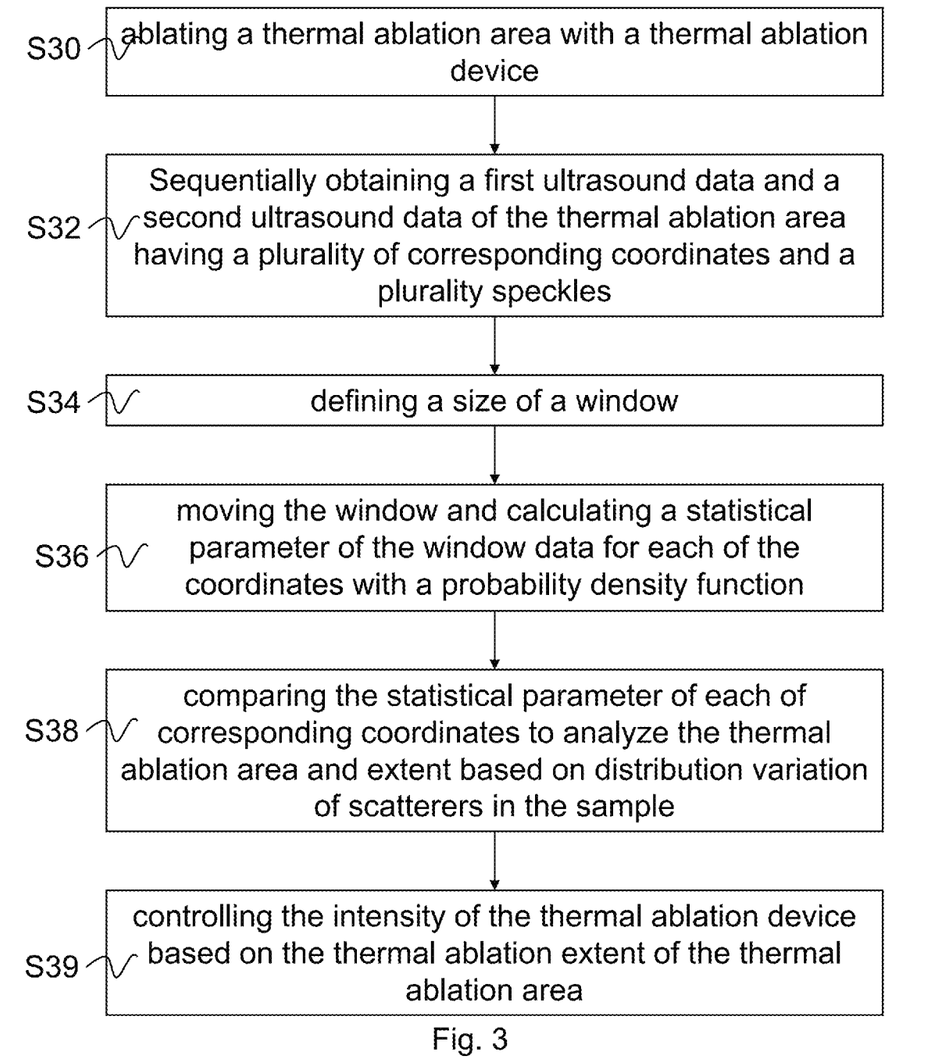
FIG. 3 is a flow chart illustrating a method for dynamically controlling thermal ablation intensity according to one embodiment of the present invention.

In addition, the present invention may be applied in monitoring non-invasive thermal ablation for tissues for controlled thermal ablation area and thermal ablation extent and reduced possible danger during medication. Refer to FIG. 3, which is a flow chart illustrating a method for dynamically controlling thermal ablation intensity according to one embodiment of the present invention. At Step S30, a thermal ablation area is thermal ablated with a thermal ablation device. At Step S32, a first ultrasound data and a second ultrasound data of a thermal ablation area are obtained in a sequential manner, wherein the first ultrasound data and the second ultrasound data respectively comprise a plurality of corresponding coordinates and a plurality speckles formed with a plurality of scatterers. At Step S34, a size of a window is defined. At Step S36, a statistical parameter for each of the coordinates is calculated by using a probability density function, wherein the statistical parameter represents the statistical distribution for signal amplitude of the speckles within the window of each of the coordinates. At Step S38, the statistical parameter of each of corresponding coordinates of the first ultrasound data and the second ultrasound data are compared to analyze the distribution variation of scatterers in the thermal ablation area to detect the precise thermal ablation area and analyze thermal ablation extent. At Step S39, the intensity of the thermal ablation device is controlled based on the thermal ablation extent of the thermal ablation area. Here the thermal ablation device may be invasive or non-invasive, for example without limitation to a HIFU (High-intensity focused ultrasound) or a laser.

The following descriptions of specific embodiments of the present invention have been presented for purposes of illustrations and description, and they are not intended to be exclusive or to limit the present invention to the precise forms disclosed, and obviously many modifications and variations are possible in light of the above teaching. It is intended that the scope of the invention be defined by the Claims appended hereto and their equivalents.

Nakagami Probability Density Function

Under Nakagami PDF, the statistical distribution model for ultrasound back-scattered packets is subject to the following equation, $$f(r) = \frac{2m^m r^{2m-1}}{\Gamma(m)\Omega^m} \exp\left(-\frac{m}{\Omega}r^2\right) U(r) \quad (1)$$

$$m = \frac{[E(R^2)]^2}{E[R^2 - E(R^2)]^2}$$

where $\Gamma(.)$ is gamma function, $U(.)$ is unit step function, $E(.)$ represents the mean value in statistics, and R represents the data size of the back-scattered envelope data, respectively. The scaling parameter $\Omega$ and Nakagami parameter m are calculated using the formula listed below, where Nakagami parameter m is a shape parameter.

Figure 4:
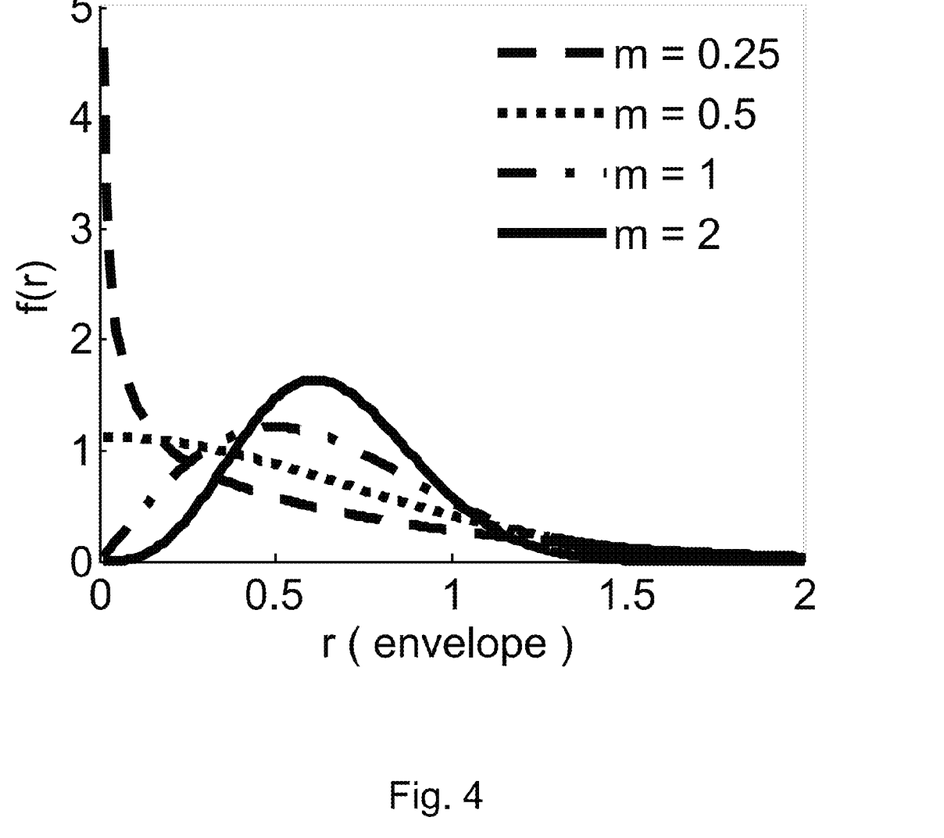
FIG. 4 is a diagram illustrating the statistical distribution of Nakagami parameter m.

Referring to FIG. 4, as m varies from 0 to 1, the statistical distribution of the envelope data would vary from pre-Rayleigh distribution to Rayleigh distribution; as m is greater than 1, the statistical distribution would lean to post-Rayleigh distribution. Therefore, different m value would correspond to different conditions for scatterers, and Nakagami distribution model is suitable for describing the statistical model for ultrasound backscattering because of its simple mathematical operation and various characteristics. Nakagami PDF has been reported by Tsui et. al (US. patent application No. 20080114242) for application in ultrasound parameter image, which is formed with m parameter of the Nakagami PDF as pixels in an image. However, the scaling parameter $\Omega$ may also have been applicable for imaging in the present invention.

Nakagami Imaging

For Nakagami imaging, the window size is firstly defined for the coordinates. Statistical distribution of partial backscattering is then calculated using the envelope data contained in the window for obtaining the m parameter of Nakagami PDF for the window area. The m value is then filled for the coordinate in the center of the window. The window then moves in an interval of one pixel and other procedures are repeated so as to obtain corresponding m values for each pixel in the image and form the Nakagami image.

Optimization of Window Size

Figure 5:
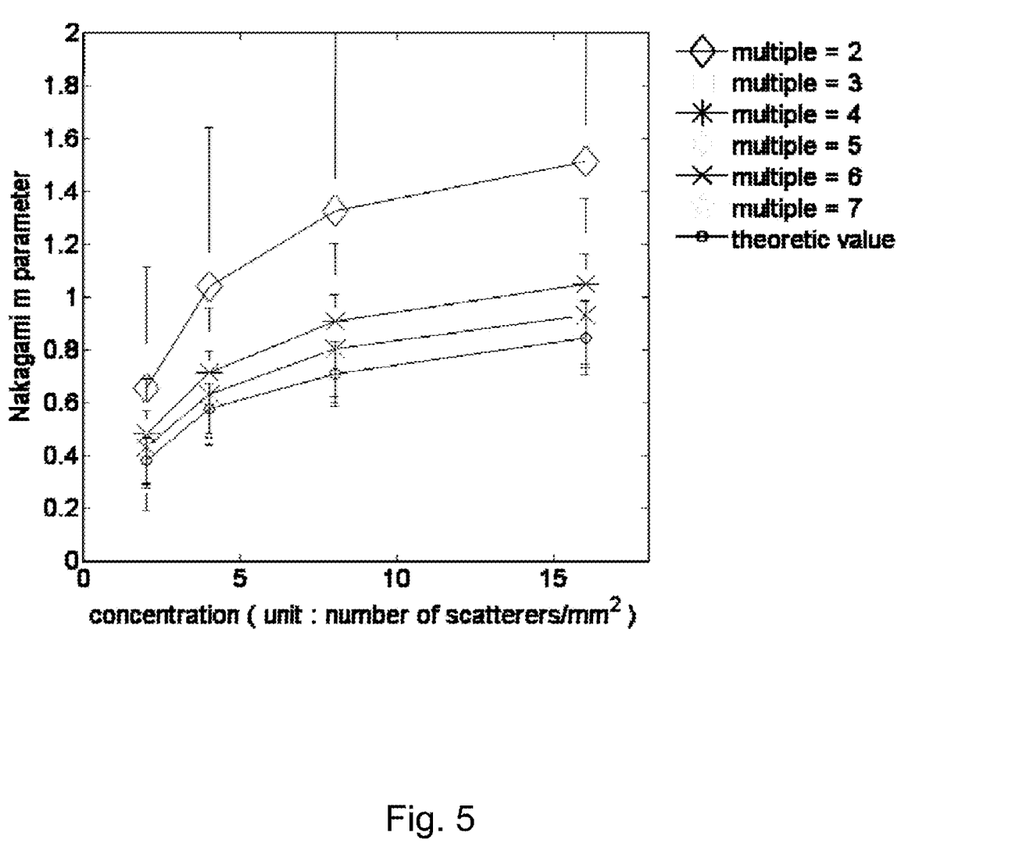
FIG. 5 is a broken line graph illustrating the correlation among window size, resolution, and precision of estimated Nakagami parameter m.

The window in the previously proposed theory is square-shaped, and has a fixed side length of 3 fold pulse length; however, the present invention proposes a different axial resolution and lateral resolution for the ultrasound imaging system. Based on axial resolution and lateral resolution of the used ultrasound imaging system, the window size is obtained with multiples of axial resolution (6 dB) and lateral resolution (6 dB) instead of square window. Referring to FIG. 5, multiples=4 may achieve both image resolution and m precision. Therefore, the length and width of the window are equal to 4-fold axial resolution and 4-fold lateral resolution, respectively for estimating partial Nakagami m parameter, and the actual length and width of the window for computing Nakagami imaging would be 1.786 and 3.4576 mm based on the system resolution for following experimental analysis.

Thermal Ablation and Ultrasound Image Capturing

A tank was filled with 30° C. degassed water and a fresh swine liver was pre-heated in the tank till 30° C. and then placed on a platform. The swine liver was then thermally ablated in an indirect manner by HIFU with 25 w and 40 w heating power. The indirect heating time was set to 1.8 second and then stopped for 1.2 second for capturing envelope data and B-mode image for further analysis. Each cycle was 3 second and there were 20 cycles (60 seconds) for the total heating time. The swine liver was then cooled for 120 second, i.e. 40 cycles, and envelope data and B-mode image was captured in each cycle. The total experimental time was 180 seconds, i.e. 60 cycles.

Comparison of Nakagami Image and B-Mode Image (1) Results of 25 w Heating Power

Figure 6A:
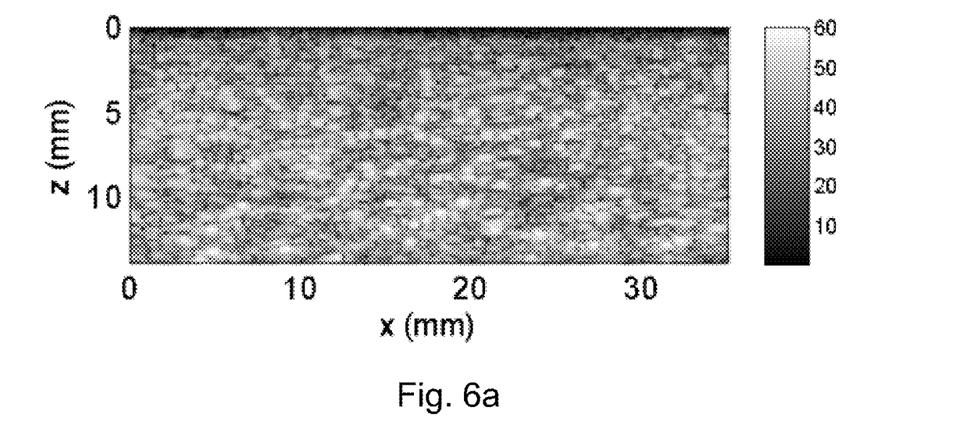
FIGS. 6a to 6f are diagrams illustrating the experiment outcome according to one embodiment of the present invention.
Figure 6B:
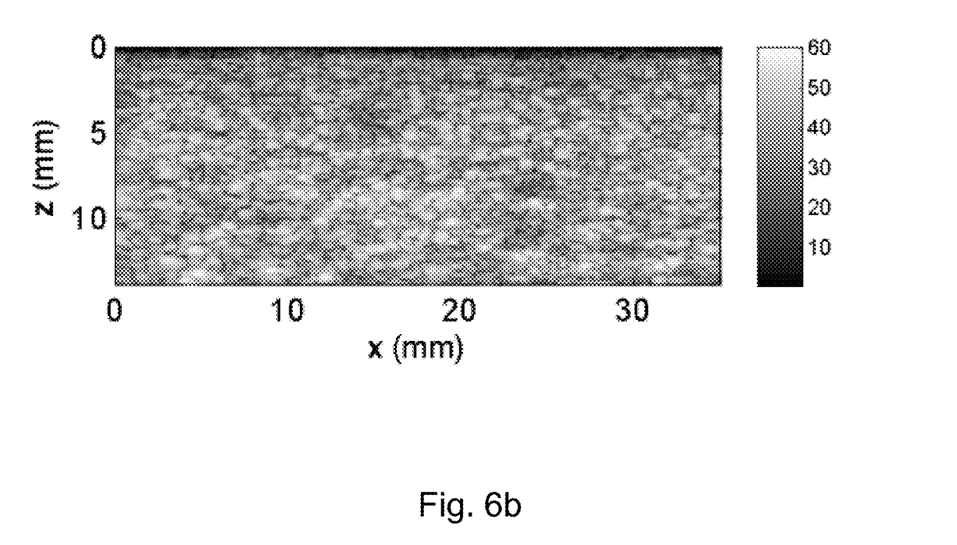
Figure 6C:
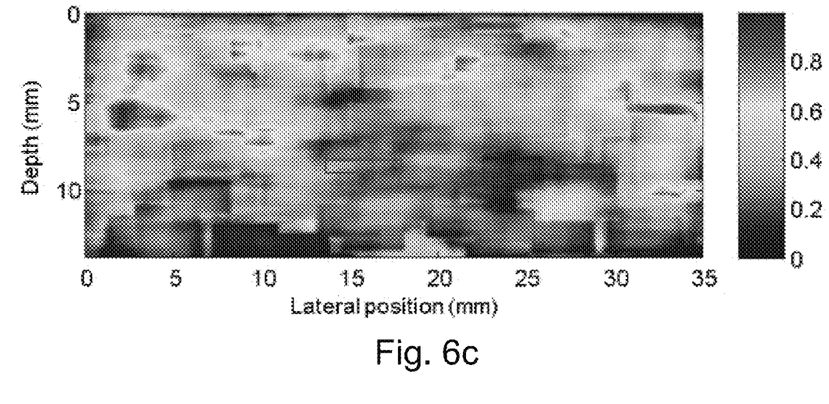
Figure 6D:
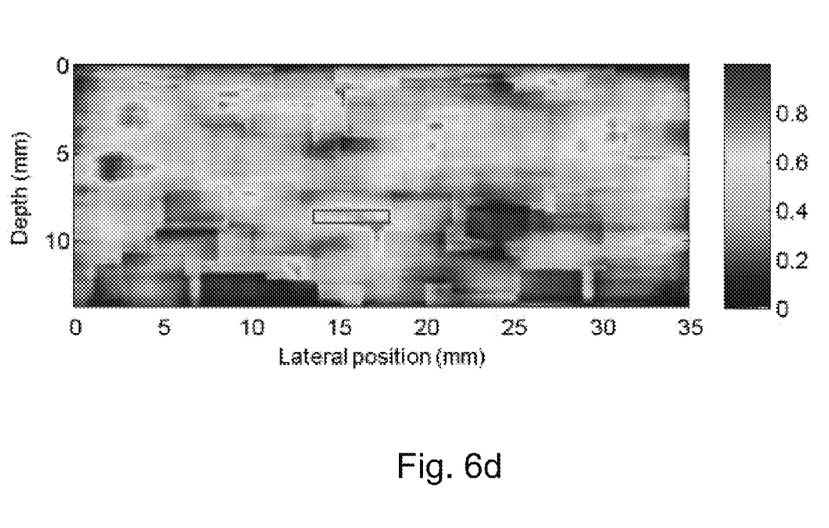
Figure 6E:
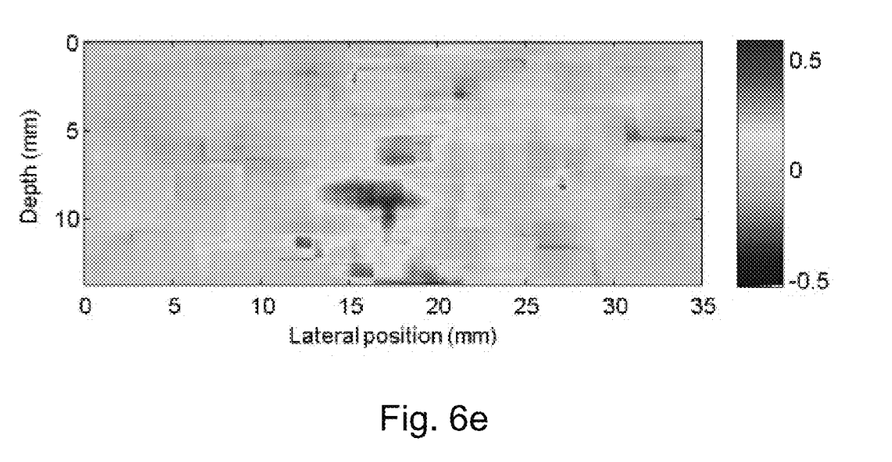
Figure 6F:
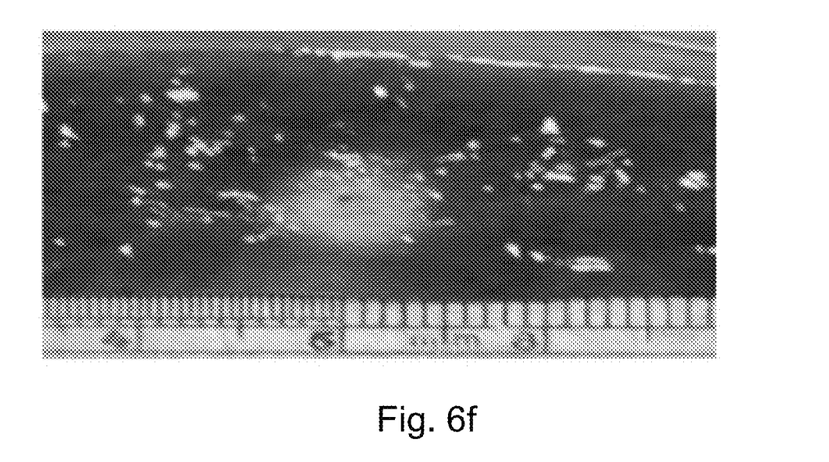

It is found that the swine liver area thermally ablated by HIFU may not be distinguished by referring to B-mode images only. Particularly, in case of no bubble formation during thermal ablation process, the thermal ablation position would be difficult to be distinguished with B-mode image. FIGS. 6a and 6b illustrate the B-mode images before and after 25 w thermal ablation for 60 seconds, and it is hard to distinguish the thermal ablation position due to no apparent bubble formation. FIG. 6c and FIG. 6d illustrate Nakagami images before and after 25 w thermal ablation for 60 seconds, where the red frame illustrates the area with obvious color changes; therefore, the Nakagami image may assist in thermal ablation identification as the B-mode image may not show when there is no apparent bubble formation. FIG. 6e illustrates the subtraction result of Nakagami images before and after thermal ablation, and the area shown with Nakagami parameter variation is fairly identical in size and position in comparison to the thermally ablated and denatured area shown in taken picture of ablated swine liver (FIG. 6f).

(2) Results of 40 w Heating Power

Figure 7A:
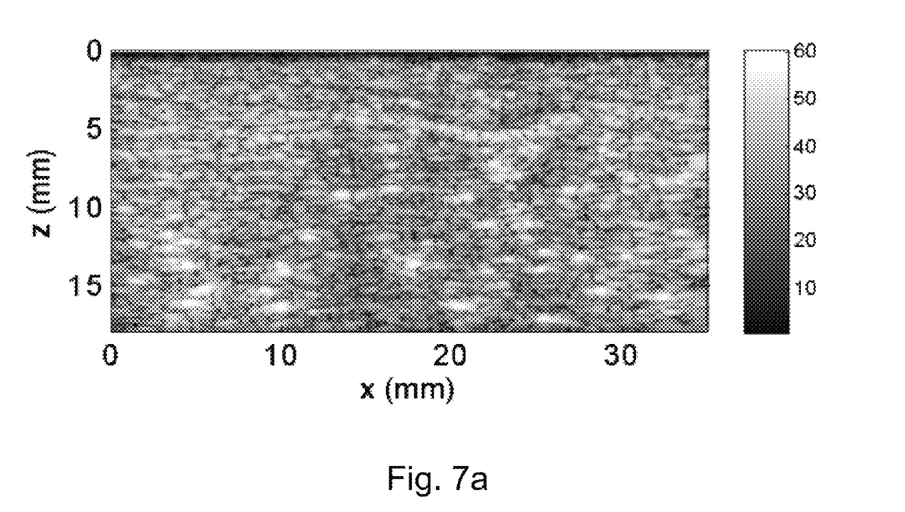
FIGS. 7a to 7f are diagrams illustrating the experiment outcome according to another embodiment of the present invention.
Figure 7B:
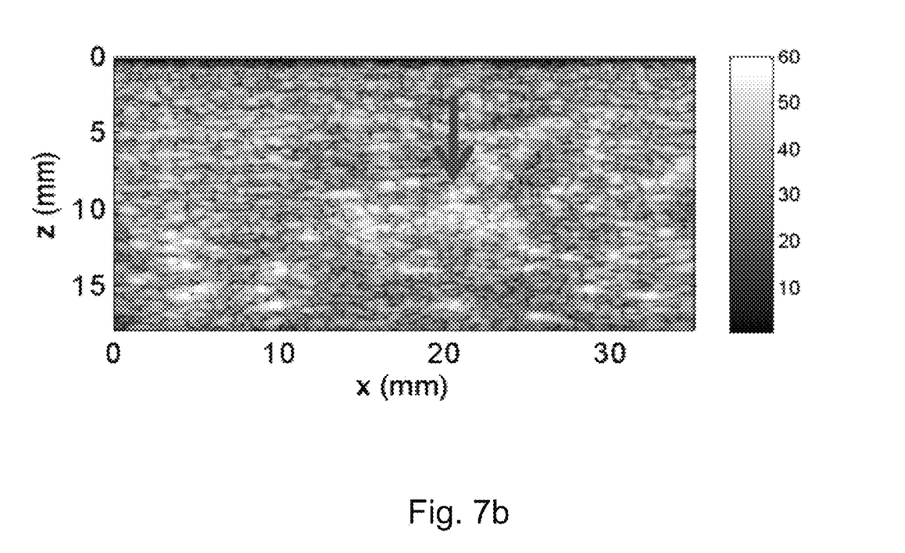
Figure 7C:
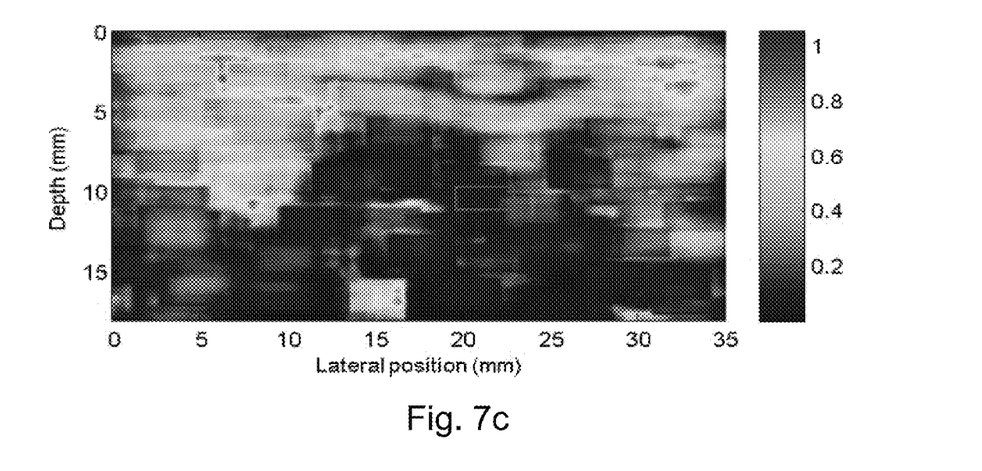
Figure 7D:
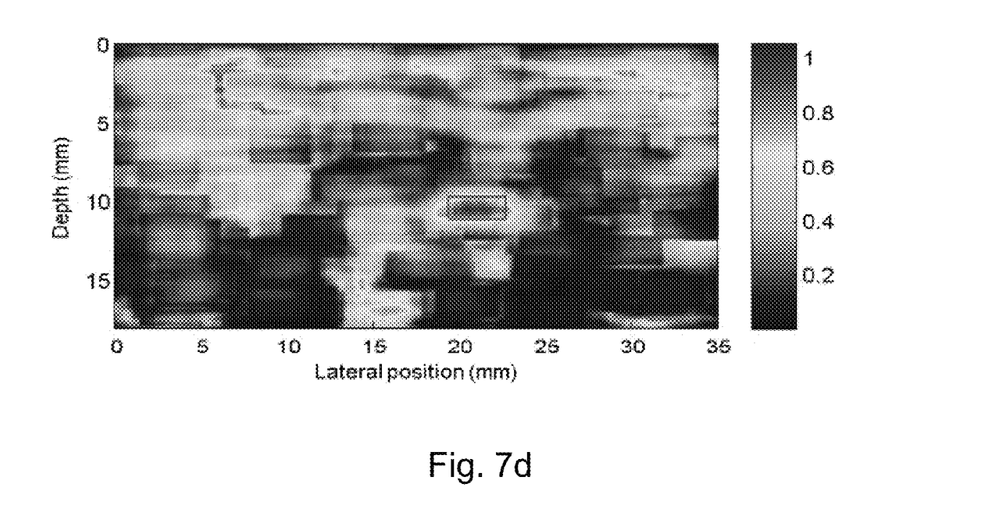
Figure 7E:
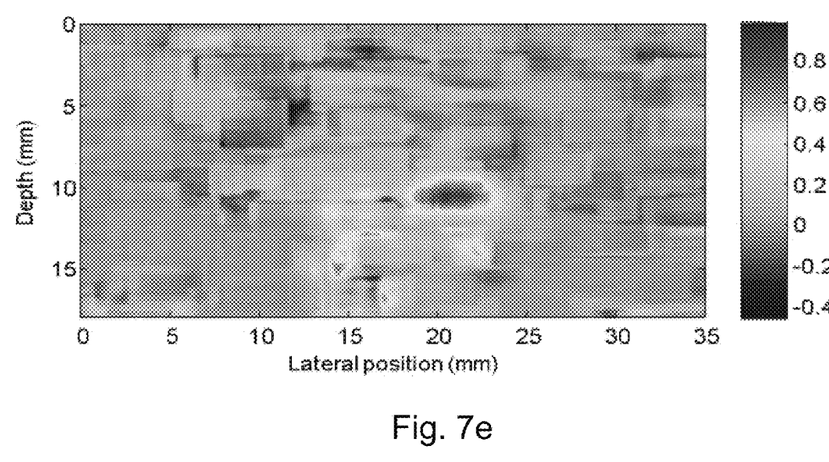
Figure 7F:
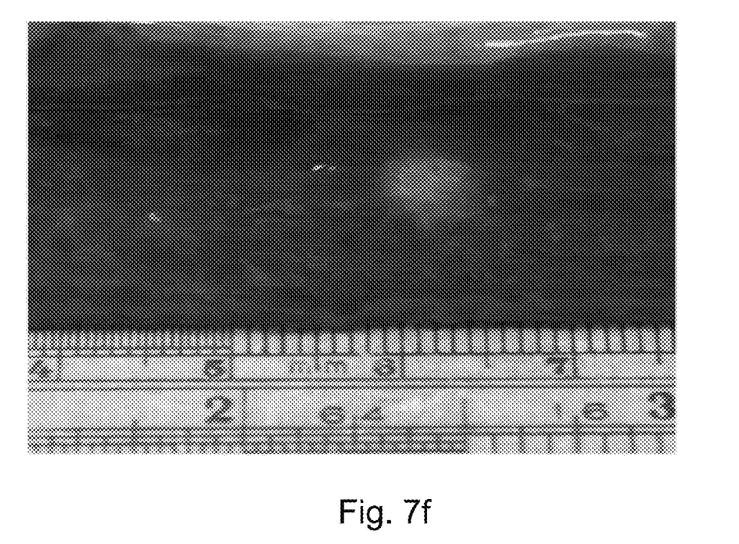

Referring to FIGS. 7a and 7b, there is bubble formation at the thermally ablated area of swine liver in the B-mode image; therefore, the thermally-ablated area may only be detected roughly but not precisely, referring to the red arrow in FIG. 7f and FIG. 7b. Instead, FIG. 7c and FIG. 7d illustrate Nakagami images before and after 40 w thermal ablation for 60 seconds, where the thermal ablation area may be distinguished with image variation. FIG. 7e illustrates the subtraction result of Nakagami images before and after thermal ablation, and the area shown with Nakagami parameter variation is fairly identical in size and position in comparison to the thermally ablated and denatured area shown in taken picture of ablated swine liver (FIG. 7f).

Therefore, Nakagami ultrasound parameter imaging may assist in thermal ablation identification as the B-mode image may not show when there is no apparent bubble formation and also precisely show the thermally ablated and denatured area with better contrast when compared to B-mode image. Furthermore, in case of bubble formation, Nakagami ultrasound parameter imaging may also precisely show the thermally ablated and denatured area with better contrast and definition when compared to B-mode image.

To sum up, the present invention is used for dynamically analyzing changes in two or three dimensional scatterer distribution and concentration of ultrasound data by using probability density function along with a moving window technique.

The present invention is achieved by defining a window size based on the resolution of ultrasound image system; moving the window; calculating a statistical parameter within the window for each of the coordinates with a probability density function, wherein the statistical parameter represents the statistical distribution for signal amplitude of the speckles within the window of each of the coordinates; and analyzing the distribution variation of scatterers in the sample. The present invention may also be used for dynamically detecting precise thermal ablation area and analyzing thermal ablation extent in a non-invasive manner and used for controlling the thermal ablation intensity.

While the invention can be subject to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:

1. A method for dynamically detecting precise thermal ablation area and analyzing thermal ablation extent, comprising:

obtaining a first ultrasound data and a second ultrasound data of a thermal ablation area in a sequential manner using an ultrasound imaging device, wherein the first ultrasound data and the second ultrasound data respectively comprise a plurality of corresponding coordinates and a plurality speckles formed with a plurality of scatterers;

defining a size of a window;

calculating a statistical parameter for each of the coordinates with a probability density function using a processor, wherein the probability density function comprises Nakagami distribution, Rayleigh model, Gaussian model, Blackman model or K-distribution model, wherein the statistical parameter represents the statistical distribution for signal amplitude of the speckles within the window of each of the coordinates; and comparing the statistical parameter of each of corresponding coordinates of the first ultrasound data and the second ultrasound data; and real-time forming a statistical parameter differential image based on the comparison result of the statistical parameters of each of the corresponding coordinates to analyze the distribution variation of scatterers in the thermal ablation area to detect the precise thermal ablation area and analyze thermal ablation extent, the real-time forming the statistical parameter differential image by comparing the Nakagami distribution, Rayleigh model, Gaussian model, Blackman model or K-distribution model with B-mode images before and after thermal ablation.

2. The method as claimed in claim 1, wherein the first ultrasound data and the second ultrasound data comprise an envelope data.

3. The method as claimed in claim 2, wherein the envelope data is converted from a radio frequency data or an image data.

4. The method as claimed in claim 1, wherein the first ultrasound data and the second ultrasound data comprise a 2D ultrasound data or a 3D ultrasound data.

5. The method as claimed in claim 1, wherein the thermal ablation area comprises bubbles or no bubbles.

6. A method for dynamically controlling thermal ablation intensity, comprising: ablating a thermal ablation area with a thermal ablation device;
   obtaining a first ultrasound data and a second ultrasound data of a thermal ablation area in a sequential manner using an ultrasound imaging device, wherein the first ultrasound data and the second ultrasound data respectively comprise a plurality of corresponding coordinates and a plurality speckles formed with a plurality of scatterers;
   defining a size of a window; calculating a statistical parameter for each of the coordinates with a probability density function using a processor, wherein the probability density function comprises Nakagami distribution, Rayleigh model, Gaussian model, Blackman model or K-distribution model, wherein the statistical parameter represents the statistical distribution for signal amplitude of the speckles within the window of each of the coordinates; comparing the statistical parameter of each of corresponding coordinates of the first ultrasound data and the second ultrasound data;
   real-time forming a statistical parameter differential image based on the comparison result of the statistical parameters of each of the corresponding coordinates to analyze the distribution variation of scatterers in the thermal ablation area to detect the precise thermal ablation area and analyze thermal ablation extent; and
   controlling the intensity of the thermal ablation device based on the thermal ablation extent of the thermal ablation area, the real-time forming the statistical parameter differential image by comparing the Nakagami distribution, Rayleigh model, Gaussian model, Blackman model or K-distribution model with B-mode images before and after thermal ablation.

7. The method as claimed in claim 6, wherein the first ultrasound data and the second ultrasound data comprise an envelope data.

8. The method as claimed in claim 7, wherein the envelope data is converted from a radio frequency data or an image data.

9. The method as claimed in claim 6, wherein the first ultrasound data and the second ultrasound data comprise a 2D ultrasound data or a 3D ultrasound data.

10. The method as claimed in claim 6, wherein the coordinates represent each pixel of the first ultrasound data and the second ultrasound data.

11. The method as claimed in claim 6, wherein the thermal ablation device is invasive or non-invasive.

12. The method as claimed in claim 6, wherein the thermal ablation device comprises a high intensity focused ultrasound or a laser.

* * * * *